United States Patent [19]

Ellis, Jr. et al.

[11] Patent Number: 5,489,716
[45] Date of Patent: Feb. 6, 1996

[54] REACTIONS CATALYZED BY HALOPORPHYRINS

[75] Inventors: Paul E. Ellis, Jr., Downingtown; James E. Lyons, Wallingford, both of Pa.

[73] Assignee: Sun Company, Inc. (R&M), Philadelphia, Pa.

[21] Appl. No.: 303,105

[22] Filed: Sep. 7, 1994

Related U.S. Application Data

[63] Continuation-in-part of Ser. No. 568,116, Aug. 16, 1990, which is a continuation-in-part of Ser. No. 425,089, Oct. 23, 1989, abandoned, which is a continuation-in-part of Ser. No. 66,666, Jun. 26, 1987, Pat. No. 4,900,871, which is a continuation-in-part of Ser. No. 246, Jan. 2, 1987, Pat. No. 4,895,682.

[51] Int. Cl.$^6$ ............................. C07C 29/50; C07C 31/12
[52] U.S. Cl. .......................... 568/910; 568/815; 568/821; 568/836; 568/838; 568/909.5; 568/909.8
[58] Field of Search ........................... 568/909.8, 910, 568/815, 821, 836, 838, 909.5

[56] References Cited

U.S. PATENT DOCUMENTS

| | | | |
|---|---|---|---|
| 4,864,041 | 9/1989 | Hill | 568/910 |
| 4,892,941 | 1/1990 | Dolphin et al. | |
| 4,895,680 | 1/1990 | Ellis et al. | |
| 4,895,682 | 1/1990 | Ellis et al. | |
| 4,900,871 | 2/1990 | Ellis et al. | |
| 4,970,348 | 11/1990 | Ellis et al. | |
| 5,118,886 | 6/1992 | Ellis et al. | |
| 5,120,882 | 6/1992 | Ellis et al. | |
| 5,120,886 | 6/1992 | Lyons et al. | 568/909.8 |
| 5,345,008 | 9/1994 | Lyons et al. | 568/909.8 |

OTHER PUBLICATIONS

Ellis et al, Cat. Lett., "Halogen Substituent Effects on the Catalytic Activity of Iron Porphyrin Complexes for Selective Air–Oxidation of Alkanes in the Liquid Phase", 3, 389–397, (1989).
Lyons et al, Cat. Lett., Selective Low Temperature Hydroxylation of Isobutane by Molecular Oxygen Catalyzed by an Iron Perhaloporphyrin Complex, 8, 45–51, (1991).
Lyons et al, J. Catalysis, Halogen Substituent Effects on the Catalytic Activity of Iron Porphyrin Complexes for the Decomposition of tert–Butyl Hydroperoxide, 141, 311–315, (1993).
Badger et al, Aust. J. Chem., "Porphyrins VII*. The Synthesis of Porphyrins By the Rothemund Reaction", 17, 1028–35, (1964).
Lindsey et al, J. Org. Chem., Investigation of the Synthesis of Ortho–Substituted Tetraphenylporphyrins, 54, 828–836, (1989).
Adler et al, J. Inorg. Nucl. Chem., On the Preparation of Metalloporphyrins*, 32, 2443–2445, (1970).
Chang et al, J.C.S. Chem. Soc. Comm., NIH Shift in Haemin–Iodosylbenzene–mediated Hydroxylations, 778–779, (1981).

Billig et al, Chem. Ind. (London), Mesomonofluorodeuteroporphyrin IX dimethyl ester, 654–655, (1969).
Naruta et al, Tetr. Lett., meso–Perfluorination of Porphyrins with N–Fluoropyridinium Triflate, 33, 1069–1072, (1992).
Onda et al, Tetr. Lett., Fluoropyrroles and Tetrafluoroporphyrins, 26, 4221–4224, (1985).
Suzuki et al., Heterocycles, Synthesis of 1–Fluoro–1–Demethylmesoporphyrin–IX, 33, 87–90, (1992).
Bonnett et al, J. Chem. Soc. (C), The meso–Reactivity of Porphyrins and Related Compounds. Part II$^1$ Halogenation, 1600–1604, (1966).
Fischer et al, Liebig's Ann. Chem., Über einige Derivate von Ätioporphyrin I, 494, 225–245, (1932).
Fischer et al, Chem. Ber., Über Tetrachlor–mesoporphyrin, 46, 2460–2466, (1913).
Gong et al, Can. J. Chem., Nitrooctaethylporphyrins: synthesis, optical and redox properties, 63, 406, (1985).
Marks et al, J. Am. Chem. Soc., Cytodeuteroporphyrin, 82, 3183–3188, (1960).
Andrews et al, J. Am. Chem. Soc., 1,4,5,8–Tetramethyl–2, 3,6,7–tetracarbethoxyporphyrin and Some Derivatives$^1$, 72, 491–494, (1950).
Fischer et al, Hoppe–Eysler's Z. Physiol. Chem., 191, Synthese einiger Prophyrine vom Ätioporphyrin III–Typ, sowie eines Tetramethyl–tripropionsäure–porphins.), 36, (1930).
Nudy et al, Tetrahedron, A Study of Bromoporphins, 40, 2359–2363, (1984).
Fischer et al, Chem–Ber., Abbau von Hämatoporphyrin zu Tetramethyl–brom–bromoxäthyl–porphrin–dipropionsäure, 60, 1861–1865, (1960).
Goff et al, J. Am. Chem. Soc., Nuclear Magnetic Resonance Investigation of Magnetic and Electronic Properties of "Intermediate Spin" Ferrous Prophyrin Complexes, 99, 3641–3646, (1977).

Primary Examiner—Joseph E. Evans
Attorney, Agent, or Firm—Q. Todd Dickinson; Stephen T. Falk

[57] ABSTRACT

The invention provides novel methods for the oxidation of hydrocarbons with oxygen-containing gas to form hydroxygroup containing compounds and for the decomposition of hydroperoxides to form hydroxygroup containing compounds. The catalysts used in the methods of the invention comprise transition metal complexes of a porphyrin ring having 1 to 12 halogen substituents on the porphyrin ring, at least one of said halogens being in a meso position and/or the catalyst containing no aryl group in a meso position. The catalyst compositions are prepared by halogenating a transition metal complex of a porphyrin. In one embodiment, a complex of a porphyrin with a metal whose porphyrin complexes are not active for oxidation of alkanes is halogenated, thereby to obtain a haloporphyrin complex of that metal, the metal is removed from the haloporphyrin complex to obtain the free base form of the haloporphyrin, and a metal such as iron whose porphyrin complexes are active for oxidation of alkanes and for the decomposition of alkyl hydroperoxides is complexed with the free base to obtain an active catalyst for oxidation of alkanes and decomposition of alkyl hydroperoxides.

2 Claims, No Drawings

REACTIONS CATALYZED BY HALOPORPHYRINS

The Government of the United States of America has rights in this invention pursuant to Cooperative Agreement No. DE-FC21-90MC26029 awarded by the U.S. Department of Energy. This application is a continuation in part of pending application Ser. No. 07/568,116 filed Aug. 16, 1990, which was a continuation in part of application Ser. No. 07/425,089, filed Oct. 23, 1989, and now abandoned, which was a continuation in pare of application Ser. No. 7/066,666, filed Jun. 26, 1987, now U.S. Pat. No. 4,900,871, which was a continuation in part of application Ser. No. 07/000,246, filed Jan. 2, 1987, now U.S. Pat. No. 4,895,682.

BACKGROUND OF THE INVENTION AND PRIOR ART

Electron deficient metalloporphyrins containing aromatic rings in meso positions (1; $R=C_6F_5$, X=F,Cl,Br, M=Fe) have been shown to be efficient catalysts for the highly selective air oxidation of light alkanes to alcohols (Ellis and Lyons, Cat. Lett., 3,389,1989; Lyons and Ellis, Cat. Lett., 8,45, 1991; U.S. Pat. Nos. 4,900,871; 4,970,348), as well as for efficient decomposition of alkyl hydroperoxide (Lyons and Ellis, J. Catalysis, 141, 311, 1993; Lyons and Ellis, U.S. Pat. No. 5,120,886). They are prepared by co-condensation of pyrrole with the appropriate aldehyde (Badger, Jones and Leslett, "Porphyrins VII. The Synthesis of Porphyrins By the Rothemund Reaction", Aust.J.Chem., 17, 1028–35, 1964 Lindsey and Wagner, "Investigation of the Synthesis of Ortho-Substituted Tetraphenylporphyrins", J.Org.Chem., 54,828, 1989; U.S. Pat. Nos. 4,970,348; 5,120,882), followed by metal insertion (Adler, Longo, Kampas and Kim, "On the preparation of metalloporphyrins", J.Inorg.Nucl.Chem., 32,2443, 1970) and 9-halogenation; (U.S. Pat. Nos. 4,892,941; 4,970,348).

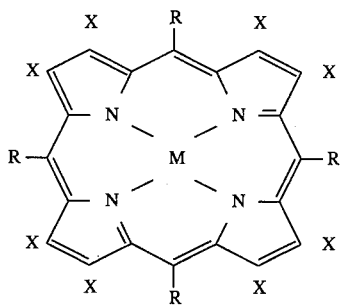

U.S. Pat. No. 4,892,941 discloses halogenated tetraphenyl porphyrins disclosed to be useful for oxidation of alkanes.

U.S. Pat. Nos. 4,895,680 and 4,895,682 disclose the use of azide and nitride transition metal ligands, i.e., coordination complexes, for the air oxidation of alkanes and other hydrocarbons.

U.S. Pat. No. 4,900,871 describes the use of iron halogenated coordination complexes for similar oxidations, disclosing that halogenating the coordination complex portion of the catalyst greatly increases the activity of the catalyst.

C. Chang and F. Ebina, J.Chem.Soc.Conn., 778 (1981)) disclose fluorinating iron and manganese tetraphenyl-porphyrinato chloride catalysts to improve their stability in the oxidation of alkanes and alkenes using strong oxidizers such as iodosylbenzene.

The following references disclose the preparation of partially halogenated porphines.

M. J. Billig et al, Chem.Ind.(London), 654 (1969) disclose mesomonofluorodeuteroporphyrin-dimethyl ester, a porphyrin having one fluorine atom in a meso position and having $-CH_3$ and $-CH_2CH_2COOCH_3$ substituents in beta positions, the remaining beta positions being unsubstituted.

Y. Naruta et al, Tetr.Lett., 33, 1069 (1992) disclose 5,10,15,20-fluorooctaethylporphines, porphyrins having fluorine atoms at 1 to 4 of the meso positions and an ethyl group at each of the beta positions.

H. Onda et al, Tetr.Lett., 26, 4221 (1985) disclose 1,3,5,7-tetrafluoro-2,4,6,8-tetramethyl porphine, a porphyrin having no meso substituents and having a fluorine atom and a $-CH_3$ group on each of the four pyrrole groups of the porphyrin.

A. Suzuki et al, Heterocycles, 33, 87 (1992) disclose 1-fluoro-2,4 -diethyl-3,5,8-trimethyl-6,7-dimethoxycarbonylethylporphine, a porphyrin unsubstituted in meso positions and containing a fluorine atom in a beta position, along with ethyl, methyl and methoxycarbonylethyl groups, also in beta positions.

R. Bonnett et al, J.Chem. Soc. 1600 (1966) disclose 5,10,15,20-chlorooctaethylporphine, 5-chlorooctaethylporphine and 5,15-dichlorooctaethylporphine, compounds which contain 1 to 4 chlorine atoms in meso positions and octaethyl groups in beta positions.

Fischer et al, Chem.Ber., 46, 2460 (1913) disclose a porphyrin containing four chlorine atoms in meso positions and alkyl groups and carboxyalkyl groups in beta positions.

Fischer et al, Liebig's Ann.Chem., 494, 225 (1932) disclose 2,7,12,17-tetraethyl-5,10,15,20-tetrachloro-3,8,13,18-tetramethyl porphine, a porphyrin having four chlorine atoms in meso positions and alkyl groups in beta positions.

Gong et al, Can.J.Chem., 63, 406 (1985) disclose 5,10,15,20-tetrachlorooctaethylporphine and 5,10-dibromo-15,20-dinitrooctaethylporphine, compounds which contain four chlorine atoms and two bromine atoms, respectively, in meso positions, and eight ethyl groups in beta positions.

G. S. Marks et al, J.Am.Chem.Soc., 82, 3183 (1960) disclose 1,2,4-tribromo-3,5,8-trimethylporphin-6,7-dipropionic acid dimethyl ester, a porphyrin unsubstituted in meso positions and containing three bromine atoms in beta positions, as well as methyl groups and propionic acid dimethyl ester groups. The same authors disclose 2,4,8-tribromo-1,3,5-trimethylporphin-6,7-dipropionic acid dimethyl ester, in which the same substituents are situated at different locations on the ring.

J. S. Andrews et al, J.Am.Chem.Soc., 72, 491 (1950) disclose 1,4,5,8-tetramethyl-2,3,6,7-tetrabromoporphine, a porphyrin having four methyl groups and four bromine atoms distributed among the four pyrrole rings.

Fischer et al, Hoppe-Eysler's Z.Physiol.Chem., 191, 36 (1930) disclose 2,7-dibromo-3,8,12,13,17,18-hexamethylporphine, a porphyrin having two bromine atoms and six methyl groups in beta positions of the porphyrin ring.

L. R. Nudy et al, Tetrahedron, 40, 2359 (1984) disclose 5-bromoporphin, 5,15-dibromoporphin and 5,10,15-tribromoporphin, a mesounsubstituted porphyrin having 1, 2 and 3 bromine atoms in beta positions.

G. F. Stephenson et al, J.Chem.Soc. 1600 (1966) disclose 5-bromooctalethylporphine, a porphyrin having one meso bromine atom, the other meso positions being unsubstituted, and eight ethyl groups in beta positions.

Fischer et al, Chem-Ber., 60, 1861 (1960) disclose 3,8-dibromodeuteroporphyrin-dimethyl ester, a meso-unsubstituted porphyrin having four methyl groups in beta positions, two bromine atoms in beta positions and two —CH$_2$CH$_2$COOCH$_3$ groups in beta positions.

Goff et al, *J.Am.Chem.Soc.*, 99, 3641 (1977) discloses Fe(II)(2,4-dibromodeuteroporphyrin dimethyl ester, a porphyrin having no meso substituents, and having two bromine atoms, three methyl groups and two —CH$_2$CH$_2$COOOCH$_3$ groups in beta positions.

DESCRIPTION OF THE INVENTION

The present invention is directed to methods for the oxidation of hydrocarbons to hydroxy-group containing compounds and for the decomposition of hydroperoxides to hydroxy-group containing compounds using as catalysts haloporphyrins containing at least one halogen atom in a meso position and/or haloporphyrins having no aryl substituents. Preferably, the haloporphyrin catalyst contains halogen atoms in all four meso positions. The beta positions of such haloporphyrins may also be substituted with 1 to 8 halogen atoms. Alternatively, the beta positions may be unsubstituted, or may be substituted with electron withdrawing groups such as nitro, cyano or halocarbyl. The catalysts used in the methods of the invention comprise transition metal complexes of haloporphines containing 1 to 12 halogen atoms in meso and/or beta positions, and/or (1) containing at least one halogen atom in a meso position or (2) containing no aryl groups in meso positions. The catalysts may comprise, in addition to the metal porphyrin complexes per se: azide derivatives thereof, hydroxide derivatives thereof where obtainable with the porphyrin configuration, and oxo-dimer derivatives thereof.

The partial oxidation of hydrocarbons and the decomposition of hydroperoxides are carried out according to the invention using catalysts which contain at least one halogen atom and which comprise a compound having the formula:

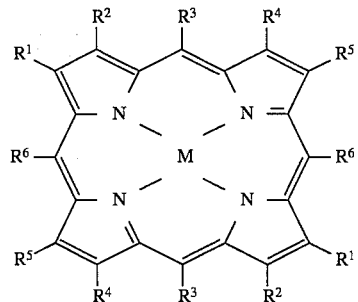

2 where at least one of the R$^3$ or R$^6$ atoms or groups is chlorine, bromine or fluorine, and the R$^1$, R$^2$, R$^3$, R$^4$, R$^5$ and R$^6$ atoms or groups are independently hydrogen, chlorine, bromine or fluorine atoms or nitro, cyano or halocarbyl groups, and M comprises transition metal, for example Fe(II) or Fe(III)X where X is halogen. Preferred compositions are those containing no unsubstituted hydrogen atoms; that is, the preferred compositions are compounds in which each of R$^1$, R$^2$, R$^3$, R$^4$, R$^5$ and R$^6$ is halogen, nitro, cyano or halocarbyl. More preferred compounds are those in which each of the above R$^1$ to R$^6$ is halogen.

Thus, in a preferred embodiment, the catalysts are perhaloporphyrins; that is, the meso-tetrahalo-beta-octahaloporphyrins (2; R$^1$=R$^2$=R$^3$=R$^4$=R$^5$=R$^6$=halogen). Examples of such compounds are meso-tetrachloro-beta-octachloroporphyrin, meso-tetrachloro-beta-octabromoporphyrin, meso-tetrafluoro-beta-octachloroporphyrin, and the like. "Perhaloporphyrin" as used herein means porphyrins in which halogen atoms are fully substituted for hydrogen atoms, or as fully substituted therefor as reasonably attainable under the circumstances.

All of the halogen atoms in the haloporphyrin may be the same halogen, for example chlorine. Alternatively, the haloporphyrin may contain more than one halogen, for example chlorine and bromine, or chlorine and fluorine, etc.

The haloporphyrin catalysts used according to the invention may be prepared by processes which involve at least one step involving halogenation of a metal complex of a porphyrin. Such step typically involves the following procedure. A porphyrin metal complex such as copper porphine (2;R$^1$=R$^2$=R$^3$=R$^4$=R$^5$=R$^6$=H, M=Cu), preferably dissolved in a solvent, for example carbon tetrachloride, is contacted with a halogenating agent, such as chlorine or bromine, at elevated temperature, for example reflux temperature. Chlorine may for example be bubbled through the solution intermittently for a prolonged period of time, for example two to five minutes every hour for twelve hours. A solution of bromine in carbon tetrachloride may alternatively be used as the halogenating agent. The product contains metal porphine complex in various degrees of halogenation, including the perhalogenated complex in which all four meso hydrogens and all eight beta hydrogens have been replaced with halogen atoms. Since the activity of transition metal, for example iron, porphyrin complexes for oxidation of hydrocarbons to alcohols, and for decomposition of hydroperoxides to alcohols, generally increases with increasing degrees of halogen substitution, it is preferred in one embodiment to separate perhalogenated metal complex from the reaction product, and convert the perhalogenated copper complex, for example, which is relatively inactive as catalyst for hydrocarbon oxidation or hydroperoxide decomposition, to a perhalogenated complex with a metal such as iron which is highly active for such oxidation and decomposition. The conversion may be accomplished for example by cooling and removing solvent from the reaction products, separating the perhaloporphyrin complex, redissolving the separated product in CH$_2$Cl$_2$, acidifying to remove copper, and inserting iron by refluxing the perhaloporphyrin with FeCl$_2$.H$_2$O.

Where compounds containing more than one halogen are desired, this may be accomplished by reacting a metal porphyrin in stages with one halogen in the one stage and another halogen in a subsequent stage. Where compounds containing both halogen and another electron-withdrawing substituent are desired, this may be accomplished by reacting a metal porphyrin in stages with halogen in one stage and another reactant such as nitrating agent in another stage.

Each of the individual reactions of the preparation of the haloporphyrin catalysts usually produces a mixture of products, from which a desired single product or range of products can be separated by selective adsorption-elution processes or other methods as known to the person skilled in the art.

OXIDATION OF HYDROCARBONS

One embodiment of the present invention provides a novel method for partially oxidizing a hydrocarbon to a hydroxy-group containing compound by contacting the hydrocarbon with oxygen and as catalyst a composition of matter as described above. The oxidation, which may be carried out in a generally known manner, is desirably conducted in the liquid phase, although this is not critical, using such organic solvents as benzene, acetic, acetonitrile, methyl acetate, or like solvents which are inert to the conditions of the reactions, or in a neat solution of the hydrocarbon if it is liquid, and under pressures ranging from about 15 to 1500 psig, preferably 30 to 750 psig, at temperature of from about 25° to 2500° C., more preferably 30° to 180° C. Depending upon whether the hydrocarbon to be oxidized is a solid, liquid or gas, it is dissolved in or bubbled through the solvent, together with air or oxygen, in the presence of the catalyst for periods of time sufficient to yield the desired oxidation product, generally from about 0.5 to 100 hours, and more preferably from 1 to 10 hours.

The choice of solvent, while not critical, can have an effect on the rates and selectivities obtained and should be selected carefully in order to optimize the desired results. For example, it has been found that solvents such as acetonitrile and acetic acid are often very effective for the oxidation of hydrocarbons to form hydroxy-group containing compounds, whereas reactions carried out in solvents such as methyl acetate or benzene may occur more slowly. Thus, by routine experimentation the optimum solvent for the particular process can be readily determined.

The ratios of the various reactants may vary widely, and are not critical. For example, the amount of catalyst employed can range from about $10^{-6}$ to $10^{-3}$ mole per mole of hydrocarbon such as alkane, and more preferably from about $10^{-5}$ to $10^{-4}$ mole of catalyst per mole of hydrocarbon, although other amounts are not precluded; while the amount of oxygen relative to the hydrocarbon starting material may also vary widely, generally the ratio is from $10^{-2}$ to $10^2$ moles of oxygen per mole of hydrocarbon. Care should be taken since some of the ratios fall within explosive limits. As a group, the catalysts are almost always soluble unless used in large excess. Thus, as a rule the reactions are generally carried out homogeneously.

The starting materials for the partial oxidation method in which the compositions according to the invention are useful include alkanes and alkenes including cycloalkanes, substituted alkanes and alkenes and the like. The starting materials thus include straight and branched chain compounds having from about 1 to 20 carbon atoms, such as methane, ethane, propane, n-butane, isobutane, n-pentane, n-hexane, 2-methylpentane, 3-methylpentane, heptane, 2-methylheptane, 3-methylheptane, the corresponding alkene forms and the like, as well as cycloalkanes and alkenes having from about 5 to 20 carbon atoms, preferably 5 to 10 carbon atoms, such as cyclopentane, cyclohexane, cycloheptane, cyclooctane, the corresponding alkene forms, and the like. These compounds, if desired, may be substituted with various moieties, although care should be taken to exclude substituents which will adversely affect the activity of the catalyst.

DECOMPOSING HYDROPEROXIDES

The present invention also provides in one embodiment a novel method for decomposing a hydroperoxide to a hydroxy-group containing compound by contacting the hydroperoxide with a catalyst comprising a composition of matter as above described.

The decomposition of hydroperoxide according to the invention is preferably carried out in a solution of the hydroperoxide, preferably a solution containing from about 5 to about 50 wt. % of hydroperoxide. Suitable solvents include benzene, chlorobenzene, o-dichlorobenzene, acetonitrile, benzonitrile, alcohols, ketones and the like. A useful solvent is the alcohol which corresponds to that formed by decomposition of the hydroperoxide, for example t-butanol formed by decomposition of t-butyl hydroperoxide.

Any suitable temperature and pressure may be used. Preferably the temperature is in the range from 0° to 200° C., more preferably 25° to 125° C. The pressure may be adjusted as necessary to accomplish decomposition; preferably 15 to 1000 psig, more preferably 15 to 100 psig. The time of reaction may be relatively short, in view of the rapid reaction rate with the catalysts employed according to the invention, but will typically be in the range from 0.1 to 5 hours, preferably 0.1 to 1 hour.

Typically, the hydroperoxide dissolved in a solvent is introduced into a reaction zone wherein it is contacted with catalyst, in the substantial absence of oxidizing agent, to convert the hydroperoxide, ROOH, where R is an organic radical, to the corresponding alcohol, ROH.

Hydroperoxides which may be decomposed according to the invention include compounds having the formula ROOH, where R is an organic radical, typically a straight or branched chain alkyl or cycloalkyl group containing 2 to 15 carbon atoms, an aryl group such as a monocyclic or polycyclic group in which the cyclic groups may optionally be substituted with one or more substituents inert to the decomposition reaction, such as alkyl or alkoxy, containing 1 to 7 carbon atoms, nitro, carboxyl or carboxyl ester containing up to about 15 carbon atoms and a halogen atom such as chlorine, bromine, or an aralkyl group in which the alkyl chain contains from 1 to 15 carbon atoms and the aryl group is as above described. Preferably R is an alkyl or cycloalkyl group containing 4 to 12 carbon atoms or an alkaryl group in which the aromatic moiety is phenyl and the alkyl substituent is straight or branched chain alkyl or cycloalkyl containing up to about 6 carbon atoms. Examples are t-butyl and isobutyl hydroperoxide, isoamyl hydroperoxide, 2-methylbutyl-2-hydroperoxide, cyclohexyl hydroperoxide, cumyl hydroperoxide, phenethyl hydroperoxide and cyclohexylphenyl hydroperoxide. Phenethyl hydroperoxide and cumyl hydroperoxide are converted to phenethyl alcohol and cumyl alcohol, respectively.

The following examples illustrate the invention:

EXAMPLE 1

Synthesis of iron perchloroporphyrin by chlorination of copper porphine, removal of copper and insertion of iron Cu porphine is dissolved in $CCl_4$ and heated to reflux. $Cl_2$ is bubbled into the very dry $CCl_4$ solution for 2–5 minutes every hour for 12 hours. After this time the solution is cooled and washed with water then evaporated to dryness. Many porphyrin products with varying amounts of chlorine incorporation are produced. Chromatography on alumina is used to recover the first band off the column eluting with $CH_2Cl_2$. This material is the perchlorinated copper porphyrin, $Cu(PCl_{12})$, copper complex of meso-tetrachloro β-octachloroporphyrin. The Cu can be removed by dissolving 100 mg of $Cu(PCl_{12})$ in 150 ml of $CH_2Cl_2$ then adding 2.5 ml of $H_2SO_4$ in 10 ml of trifluoroacetic acid. After 10 minutes of stirring the $H_2PCl_{12}$, meso-tetrachloro-β-octachloroporphine, is recovered by extraction with CH2C12 and sodium bicarbonate wash. Iron is inserted into the $H_2PCl_{12}$ by refluxing the porphyrin in tetrahydrofuran with an excess of $FeCl_2.4H_2O$. After chromatography and treatment with HCl, $Fe(PCl_{12})Cl$, an iron complex of meso-tetrachloro-β-octachloroporphyrin is obtained.

EXAMPLE 2

Partial oxidation of isobutane with an iron complex of meso-tetrachloro-β-octachloroporphyrin as the catalyst The catalyst prepared in Example 1 is dissolved in benzene (25 ml) and isobutane (7 g) added. Oxygen (5 bars) is pressed on the stirred solution at 60° C. for six hours. After this time, the solution is cooled and brought to atmospheric pressure. The main product is tert-butyl alcohol, acetone and di-tert-butylperoxide being minor products.

EXAMPLE 3

Decomposition of hydroperoxide with an iron complex of meso-tetrachloro-β-octachloroporphyrin as the catalyst The complex prepared in Example 1 is directly added to a stirring solution of tert-butylhydroperoxide (TBHP, 13.8 g) in tert-butyl alcohol (TDA, 18.1 g) at 80° C. Oxygen is rapidly evolved and the TBHP converted largely to TBA, acetone and di-tert-butylperoxide being minor products.

The invention claimed is:

1. Method of partially oxidizing hydrocarbons which comprises contacting a hydrocarbon under partial oxidation conditions with oxygen and a catalyst comprising a compound having the formula:

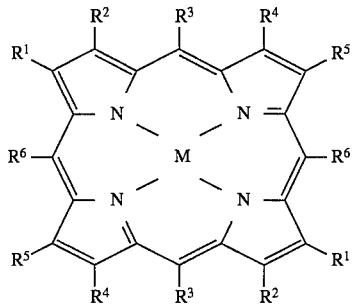

where at least one of said $R^3$ or $R^6$ atoms or groups is chlorine, bromine or fluorine, and said $R^1$, $R^2$, $R^3$, $R^4$, $R^5$ and $R^6$ atoms or groups are independently hydrogen, chlorine, bromine or fluorine atoms or nitro, cyano or halocarbyl groups, and M comprises transition metal, or an oxobridged dimer of said compound, or an azide of said compound.

2. Method according to claim 1 wherein said transition metal comprises iron.

* * * * *